US012774443B2

(12) United States Patent
Von Guttenberg et al.

(10) Patent No.: US 12,774,443 B2
(45) Date of Patent: Oct. 27, 2026

(54) CELL CULTURE CARRIER

(71) Applicants: ibidi GmbH, Gräfelfing (DE); Technische Universität Darmstadt, Darmstadt (DE)

(72) Inventors: Zeno Von Guttenberg, Gröbenzell (DE); Anna Fritschen, Darmstadt (DE); Andreas Bläser, Troisdorf (DE)

(73) Assignees: ibidi GmbH, Gräfelfing (DE); Technische Universität Darmstadt, Darmstadt (DE)

( * ) Notice: Subject to any disclaimer, the term of this patent is extended or adjusted under 35 U.S.C. 154(b) by 546 days.

(21) Appl. No.: 18/329,802

(22) Filed: Jun. 6, 2023

(65) Prior Publication Data

US 2023/0392104 A1 Dec. 7, 2023

(30) Foreign Application Priority Data

Jun. 7, 2022 (EP) .................................... 22177581

(51) Int. Cl.
*C12M 1/00* (2006.01)
*C12M 1/12* (2006.01)

(52) U.S. Cl.
CPC ............ *C12M 29/10* (2013.01); *C12M 23/06* (2013.01); *C12M 23/50* (2013.01); *C12M 23/52* (2013.01); *C12M 25/04* (2013.01); *C12M 37/04* (2013.01)

(58) Field of Classification Search
CPC ...... C12M 29/10; C12M 23/06; C12M 23/50; C12M 23/52; C12M 25/04; C12M 37/04; C12M 23/34; C12M 23/40; C12M 23/16
See application file for complete search history.

(56) References Cited

U.S. PATENT DOCUMENTS

| | | | | |
|---|---|---|---|---|
| 2006/0099705 A1* | 5/2006 | Wikswo | C12M 29/10 435/297.5 |
| 2007/0272000 A1 | 11/2007 | Kahl et al. | |
| 2017/0022464 A1* | 1/2017 | Novak | G01N 33/5005 |

FOREIGN PATENT DOCUMENTS

| | | | | |
|---|---|---|---|---|
| DE | 10 2020 107599 B3 | 7/2021 | |
| EP | 2 681 306 B1 | 1/2019 | |
| EP | 3 907 007 A1 | 11/2021 | |
| WO | 2012/050981 A1 | 4/2012 | |
| WO | 2016/076795 A1 | 5/2016 | |
| WO | WO-2020252225 A1 * | 12/2020 | C12N 5/0012 |
| WO | WO-2021165025 A1 * | 8/2021 | C12M 23/22 |
| WO | WO-2023073178 A1 * | 5/2023 | C12M 29/10 |

* cited by examiner

*Primary Examiner* — Liban M Hassan
(74) *Attorney, Agent, or Firm* — Lowenstein Sandler LLP

(57) ABSTRACT

The invention relates to a cell culture carrier comprising a first channel and a reservoir, where the first channel and the reservoir are formed in the interior of the cell culture carrier, where the first channel has an inlet opening in an outer side of the cell culture carrier and an outlet opening in the outer side of the cell culture carrier, where the reservoir has at least two openings arranged next to one another, where the first channel is connected to the reservoir by the at least two openings, and where the reservoir is connected to the outer side of the cell culture carrier by no other channel.

15 Claims, 7 Drawing Sheets

CELL CULTURE CARRIER

CROSS-REFERENCE TO RELATED APPLICATION

The present application claims priority under 35 U.S.C. § 111(a) to EP Application No. 22177581.0, filed Jun. 7, 2022, which is incorporated herein by reference in its entirety.

The present invention relates to a cell culture carrier, a cell culture carrier kit, and a method for introducing cells or cell aggregates into such a cell culture carrier.

BACKGROUND

Cell culture carriers are used, among other things, to simulate and examine the growth and behavior of living cells under controlled environmental influences. To do this, the cells must be held in a defined volume, for example, a cavity in the cell culture carrier, in order to be able to observe them there using, for example, microscopy. During the cultivation and examination, the cells are typically supplied with nutrients by way of a cell medium. It is important, in particular when replacing this cell medium, that the cells are neither exposed to a direct flow nor flushed out of the volume mentioned.

A basic distinction is made between two different cell types, adherent and non-adherent cells Adherent cells can adhere to a surface or substrate, where the nature of the surface has an impact on the cell's ability to adhere. Adherent cells are not detached from the surface when the cell medium is exchanged. If cells cannot adhere to a surface, they form cell aggregates, so-called spheroids, by adhesion to one another. Accordingly, the latter are not connected to the surface and are moved away by a flow from a cell medium.

The physiological behavior of the cells also depends on whether they are present adhering or being suspended in the cell medium. Certain cells, such as immune cells, can change their properties due to contact with a surface. Consequently, if it is desired to observe cells over longer periods of time, non-adherent cells must be held in one place without being moved along when the cell medium is exchanged. In examinations that are to be carried out on spheroids, adherent cells must at the same time be prevented from adhering to a surface since the cell aggregate would otherwise restructure itself to form a cell layer. Furthermore, very few cells in natural organ structures come into direct contact with a blood stream and are therefore not exposed to shear stress. They commonly obtain their nutrients by diffusion through intracellular tissue. In order to create physiological conditions, these cells in a cell culture carrier must accordingly not be exposed to any direct flow of the cell medium, i.e. they must not be perfused.

A microfluidic platform for investigating cell-based interactions comprising three microfluidic channels arranged next to one another is known from WO 2016/076795 A1. Fluid exchange takes place between the central channel and the respective channels arranged on the outer side so that a cell medium can be exchanged between the channels. The center channel is filled with hydrogel or extracellular matrix in which cells reside. The center channel comprises regions that have no connection to the other channels so that there is no contact with the cell medium in these regions. This pertains in particular to the sections between the channel mouth in the outer side of the platform and the section where a connection is established to the other two channels. Cells disposed in said regions cannot be supplied with nutrients, or not sufficiently, and therefore die off. For this reason, there are unused regions in this channel where biological examinations cannot be conducted. The regions can therefore be referred to as dead regions.

BRIEF SUMMARY

In the light of these drawbacks, it is an object of the present invention to provide a cell culture carrier as well as an associated cell culture carrier kit and a method for introducing cells or cell aggregates into such a cell culture carrier in which no dead regions form or the formation of dead regions is suppressed so that a volume available for the examination of cells can be fully utilized.

This object is satisfied by the cell culture carrier according to claim 1, the cell culture carrier kit according to claim 11, and the method according to claim 13. Particularly advantageous developments can be found in the associated dependent claims.

According to the invention, a cell culture carrier is provided comprising a first channel and a reservoir, where the first channel and the reservoir are formed in the interior of the cell culture carrier, where the first channel has an inlet opening in an outer side of the cell culture carrier and an outlet opening in the outer side of the cell culture carrier, where the reservoir has at least two openings arranged next to one another, where the first channel is connected to the reservoir by the at least two openings, and where the reservoir is connected to the outer side of the cell culture carrier by no other channel.

A cell medium flowing through the channel can reach the reservoir through the openings between the reservoir and the channel and be distributed there. The reservoir is connected to an outer side of the cell culture carrier only via the channel, because there is no channel that opens directly into the reservoir. Cells or cell aggregates disposed in the reservoir are therefore spatially restricted to the region of the reservoir and the above-mentioned sections between a channel mouth and the reservoir do not arise. In particular, the cells are restricted to a region that can be supplied with the cell medium so that the entire reservoir can be used for the examination of cells.

The outer side of the cell culture carrier is presently referred to as all of its outwardly facing surfaces. In particular, the inner surfaces of the channel and the reservoir are not comprised by this.

A channel is, for example, a tube formed in the cell culture carrier. A channel comprises two openings or apertures, which in the present case are the inlet opening and the outlet opening. Both openings are arranged in an outer side of the cell culture carrier and can there be formed, for example, as a hole in the outer side.

The channel can have a diameter or a width of a cross section, respectively, that is smaller than the length of the channel. In this case, the length can be the distance between the inlet opening and the outlet opening of the channel, where passing through it from its inlet opening to its outlet opening determines the length of a channel. The ratio between the width of a cross section and the length of a channel can then have a value of 0.2 or less, in particular 0.1 or less, in particular 0.05 or less. A reservoir, on the other hand, can have a diameter or a width that is greater than the height of the reservoir. The height of the reservoir is the vertical distance between defining surfaces of the reservoir. The ratio between the width of the reservoir and the height of the reservoir can have a value of 2 or more, in particular 5 or more, in particular 10 or more.

Since a medium flows through the channel between the inlet opening and the outlet opening, the openings by which the channel is connected to the reservoir are not disposed in the direction of flow of a medium flowing through the channel. The openings can be arranged, in particular, laterally in the channel. The medium therefore flows substantially past the openings and an exchange with the interior of the reservoir only takes place by way of diffusion as a result of a concentration gradient between the channel and the reservoir and not by way of a direct flow. In particular, the channel can be arranged such that it is tangent to the reservoir or runs along a certain section parallel to the side wall of the reservoir.

Different embodiments, in particular geometric shapes, are possible for the reservoir as a cavity in the cell culture carrier. For example, it can have a cylindrical shape. The openings can be arranged in the jacket surface of the cylinder. Instead of a cylinder, the reservoir can also have the shape of a prism. In this case, a side surface of the reservoir can also be defined, in analogy to the jacket surface of a cylinder. In particular, the openings can be arranged in the side surface of the reservoir. In addition, it is possible for the reservoir to have the shape of a sphere or an ellipsoid of revolution.

The cell culture carrier can comprise exactly one channel.

The reservoir of the cell culture carrier can be connected to exactly one channel.

It arises from these formulations that the reservoir is connected to the outer side of the cell culture carrier via no other channel.

The reservoir can furthermore have a circular, elliptical, or rectangular cross-sectional area. A ratio of two main extensions of the cross section of the reservoir can be in the range between 0.5 and 2, where the cross section is defined by a plane which is disposed parallel to a base area of the cell culture carrier.

A circular or elliptical cross-sectional shape of the reservoir allows for reliable distribution of a cell culture medium (hereinafter also referred to as cell medium) in the reservoir, which is transported through the openings into the reservoir by diffusion. This additionally contributes to the fact that dead regions, in which an exchange of the cell medium takes place only over long-time scales, can be prevented. Furthermore, a round or elliptical shape provides the advantage that the ratio of surface to volume is particularly low. A smaller surface region reduces the likelihood of cells adhering to the walls of the reservoir.

A rectangular cross-sectional shape allows for a particularly simple geometry for the arrangement of the reservoir and the channel. In particular, the channel can run in a straight line and parallel to a side of the rectangle and can have a plurality of openings, in particular more than two openings, along the side of the rectangle. Several openings allow for more reliable and faster exchange of medium between the channel and the reservoir.

A smaller volume of the reservoir than in prior art can be enabled, while the exchange of the cell medium takes place efficiently by the selection of the main extensions of the cross section. A small reservoir volume has the advantage that a smaller number of cells and a smaller amount of additional materials such as hydrogels have to be used for the examinations. In this way, the costs for experimental examinations can be reduced. Depending on the shape of the reservoir and the arrangement and number of openings, the cell medium can also be exchanged in a small volume within a shorter period of time and the supply of nutrients to cells in the reservoir can be improved.

A main extension can be understood to mean a maximum or a characteristic length of the geometric cross-sectional shape. In the case of an elliptical cross section, the two main extensions correspond to the major and minor semi-axes of the ellipse. The reservoir can also have a rectangular cross section. In this case, the main extensions would be the lengths of the sides of the rectangle. However, the shape of the cross section is not restricted to the examples mentioned and can be of any desired design since main extensions can be defined for any geometric shape.

The cell culture carrier can have a base area which can be formed to be, in particular, planar. When used as intended, the base area forms the underside of the cell culture carrier. Unless otherwise specified, all information that relates directly or indirectly to the cell culture carrier and the spatial arrangement of its components, i.e. for example “above”, “below”, “at the top” or “at the bottom” is to be understood to be with reference to the base area of the cell culture carrier.

The cell culture carrier can comprise a second channel, where the second channel is connected to the reservoir by at least two further openings.

The formation of a second channel in the cell culture carrier increases the flexibility and possible uses thereof. For example, a different medium con flow through the second channel than through the first channel. By connecting the reservoir to a second channel, the exchange rate of a medium between the channels and the reservoir increases so that the exchange of the cell medium between the channels and the reservoir can take place in a shorter period of time than in the case of only a single channel. In this way, for example, cells in the reservoir can be better supplied with nutrients.

The cell culture carrier can comprise exactly two channels, namely the first channel and the second channel.

The reservoir of the cell culture carrier can be connected only to the first channel and the second channel.

It also arises for the special cases mentioned of the channel comprising exactly one or exactly two channels that the reservoir is connected to the outer side of the cell culture carrier by no other channel than the first channel and the second channel. In other words, the cell culture carrier comprises no channel that ends in the reservoir or the reservoir is only connected to channels that have exactly two openings on the outer side of the cell culture carrier, in particular an inlet opening and an outlet opening.

The openings between the reservoir and the first channel and the reservoir and the second channel can be arranged at oppositely disposed points in the reservoir.

Forming openings connecting the channels to the reservoir at oppositely disposed points of the reservoir allows for improved fluid exchange between the channels and the reservoir. Furthermore, a larger number of openings also reduces the possibility that dead regions, in which the exchange of the cell medium between the channels and the reservoir does not take place or only takes place over long time scales, can form in the reservoir.

The term “oppositely disposed” in this context means that the two points are arranged in different regions of the reservoir. For example, the regions can be arranged on different sides of a central axis of the reservoir. In the case of a rectangular reservoir cross section, one of said points can be arranged on each of the two sides of the rectangle extending in parallel. Two semicircles can be defined for a circular cross section, where the two points are arranged in different semicircles. An analogous definition can also be applied to an ellipse. In a special case, the points at which the openings are formed can be connected in a straight line by an imaginary line, where the line runs through the geometric center of the reservoir.

A distance between two of the at least two adjacent openings can be greater than half the value of a width of the openings. A distance between two of the at least two adjacent openings can be smaller than five times the value of the width of the openings.

Openings arranged close to one another in the manner described can provide a larger quantity of medium in a defined region in the reservoir. For example, regions with a higher nutrient concentration can be obtained when a cell medium flows through the channel, which can favor the cells in the relevant regions in the reservoir.

The reservoir can be coated in part or entirely with a cell-repellent layer.

Such a cell-repellent layer can ensure that cells in the reservoir cannot adhere to an inner wall, for example, the side wall. As described, adhesion of cells to the inner wall of the reservoir can change their properties, which can be prevented by a cell-repellent layer.

In a simple case, a cell-repellent layer can already be formed by untreated plastic material because cells typically adhere poorly to hydrophobic surfaces. However, coatings made of polymers, proteins, and lipids, which can be applied to an inner wall of the reservoir, are also suitable for the cell-repellent layer. In this case, the inner wall of the reservoir comprises all surfaces of the reservoir. The entire inner surface can be coated with the cell-repellent layer, but it is also possible for only certain parts or sections of said inner surface to be coated with the cell-repellent layer.

The cell culture carrier can comprise a cover element and a base element, where a trench and a depression are formed on the side of the cover element facing the base element, where the cover element and the base element are connected to one another in a planar manner such that the trench and the depression are covered with the base element, and where the channel is formed by covering the trench and the reservoir is formed by covering the depression.

The use of a base element simplifies the manufacture of the cell culture carrier. For example, the cover element can be manufactured by way of injection molding, which is a simple, precise, and inexpensive manufacturing method. While no cavities can be formed in a component to be manufactured by injection molding, the formation of a depression and/or a trench on a surface represents a simple alternative for obtaining an equivalent cell culture carrier in combination with a base element for covering the depression and the trench. A further advantage of dividing the cell culture carrier into a cover element and a base element is evident in the context of its use. Cells to be examined can be introduced directly into the depression before the reservoir is formed by the closure with the base element.

The trench can also adjoin a channel formed as a tube within the cover element so that the entire channel is formed by the tube in connection with the trench covered with the base element. Finally, the entire channel is formed in the cell culture carrier by covering the trench with the base element. In this context, covering is understood to mean, in particular, a liquid-tight closure of the trench by the base element. As a result, a medium, in particular a liquid, can flow through the channel formed in this manner without being able to exit at points other than the inlet opening and the outlet opening.

The depression formed in the cover element is also covered with the base element in the same way as the trench. This forms the reservoir, which represents a cavity within the cell culture carrier.

This composition of a cell culture carrier with a cover element and a base element can be combined with the properties of the cell culture carrier described above. For example, the cell culture carrier can comprise more than one channel, where correspondingly more than one trench can be formed in the side of the cover element. In particular, a trench can be formed in the side of the cover element for each channel of the cell culture carrier, but fewer trenches than there are channels can also be present in the cell culture carrier. The shapes of the reservoir described, to the extent that they are compatible with this embodiment of the cell culture carrier, can also apply to the cell culture carrier comprising a base element and a cover element.

The cell culture carrier described can furthermore comprise an adhesive film which is arranged between the cover element and the base element so that the cover element and the base element are connected and adhesively bonded to one another in a planar manner.

There are several ways to connect the cover element to the base element. The use of an adhesive film represents a particularly simple, user-friendly, and inexpensive option, although a stable and lasting connection of the cover element to the base element is obtained at the same time. In this specification, several options for the formation of the adhesive film shall be presented hereafter.

The adhesive film can be arranged on the side of the surface of the cover element in which the depression and the trench are also formed. This side faces the base element. The adhesive film does not cover, in particular, the depression. In particular, it is also possible for the adhesive film to cover neither the depression nor the channel. The adhesive film can cover the entire remaining area, but it can also be applied only in individual sections, as long as the result is that the cover element and the base element are firmly adhesively bonded to one another. The adhesive film can have a thickness between 50 μm and 500 μm, in particular between 50 μm and 150 μm.

The cell culture carrier can consist of the cover element, the base element, and the adhesive film, i.e, not comprise any further components.

Two of the at least two openings of the first channel arranged next to one another can be separated by a column, where the column is formed in the cover element and touches the base element, and where the side of the base element facing the cover element is formed to be planar.

Since the column touches the base element, there are no gaps or other spacings present between the column and the base element through which cells can escape from the reservoir. There is therefore additional security in that the cells are enclosed within the reservoir and can be retained therein.

It is to be noted that the column cannot be covered with the adhesive film since it touches and is in contact with the base element.

If the cell culture carrier comprises a second channel, then two of the at least two openings of the second channel arranged next to one another can also be separated by a column.

When the cell culture carrier is used as intended, microscopy can be carried out on the cell culture carrier through the base element. This shall be discussed hereafter in more detail. In this case, a side of the base element formed to be planar is advantageous for optical examinations since it suppresses optical imperfections as compared to a contoured side. In particular, the side of the base element facing away from the cover element can also be formed to be planar, i.e. these two sides can be planar and parallel.

The column can have a circular cross section along its longitudinal axis which is particularly easy and precise to produce in the framework of injection molding as a manufacturing technique. The diameter of the columns can be between 20 μm and 500 μm. However, the cross section can also have a different shape, without the technical problem solved by the present cell culture carrier being impaired thereby. For example, an elliptical or rectangular cross section can also be envisaged. The size scale mentioned for the cross section can also be applied correspondingly to other cross-sectional shapes.

The height of the column can be greater than the height of the depression in the cover element. The height of the depression is the vertical distance between the base of the depression and the side of the surface of the cover element in which the depression is formed. The column can therefore project beyond the surface of the cover element in particular, the difference between the height of the column and the height of the depression can correspond to the thickness of the adhesive film. It can thus be ensured that the cover element and the base element are connected to one another, that is to say touch one another, without creating undesirable gaps or spacings between the two elements through which cells could escape from the reservoir. At the same time, this also means that the column cannot be covered with the adhesive film.

The reservoir can have more than two adjacent openings. Since a column can be placed between two adjacent openings to separate them, more than one column can also be present in this case. If N denotes the number of openings, then correspondingly N−1 columns can be formed which separate these N openings from one another. One column of these N−1 columns can touch the base element, but it is also possible for several or all of the columns to touch the base element, or to establish direct contact with the base element.

The medium exchange between the channel or the channels, respectively, and the reservoir is improved by a plurality of openings, while at the same time there is no increased risk that the cells can escape from the reservoir.

Furthermore, the openings arranged next to one another in the side wall can be separated by a plurality of columns, where the plurality of columns is arranged in the form of a grid. In particular, the grid can be a two-dimensional grid. In this case, a series of columns arranged next to one another that are closest to the reservoir defines the openings of the reservoir. The number of openings in the reservoir is therefore not changed by the arrangement of the columns in a two-dimensional grid. Further columns of the plurality of columns are consequently disposed further away from the reservoir. A grid is presently understood to mean a regular arrangement of the columns, where the positions of the columns are arranged to be translationally symmetrical. For example, the columns can be arranged in a square, triangular, or hexagonal grid. Furthermore, some of the columns farther from the reservoir can be arranged in the channel.

The openings can be formed to be so narrow that cells or cell aggregates in the reservoir cannot escape therefrom and therefore cannot reach the channel. This can be accomplished, for example, in that the distance between the columns and therefore the width of the openings is smaller than the typical size scale of the cells or cell aggregates disposed in the reservoir. A plurality of columns arranged in a grid further reduces the possibility because further narrowings are formed in addition to the openings through which the cells would have to pass.

The reservoir of the cell culture carrier can be filled with a gel containing cells or cell aggregates.

By providing a cell culture carrier filled with gel, a user of the cell culture carrier can employ it directly for the intended use. For example, the cell culture carrier can be used to retain and examine non-adherent cells in the reservoir, for example, by way of microscopy. A cell medium can flow through the channel and enter the reservoir by diffusion through the openings and the cell medium is exchanged accordingly, without the cells being exposed to a direct flow. As a result, the cells or cell aggregates are not exposed to any shear stress. This has the advantage of achieving a physiological state, since only a few cell types, such as endothelial cells, are exposed to a flow in the human body, while most types of cells absorb nutrients by diffusion. This situation has a high physiological relevance, it therefore comes very close to scenarios that occur in nature.

In particular, the gel can be a hydrogel which corresponds to a gel made of crosslinked polymers which can bind water. It can comprise or be made of the materials GelMA, alginate, collagen, or fibrin. When selecting the material, it is important to note that it must be able to be crosslinked accordingly for forming a gel. For example, collagen can be crosslinked by thermal influence. On the other hand, alginate can be chemically cross-linked whereas GelMA can be cross-linked by UV radiation. In the case of fibrin, a gel can be created enzymatically by thrombin. The cells can be contained homogeneously in the gel or surrounded thereby in cell aggregates. The advantage of a hydrogel is that it can be used to realistically simulate mechanical and hydrodynamic conditions in tissue. The nutrients from the cell culture medium can also easily diffuse through a hydrogel to the cells.

The distance between the columns and therefore the width of the openings can be made to depend on the nature of the gel, in particular its viscosity. The distance between two adjacent columns can be between 50 μm and 500 μm, in particular between 100 μm and 300 μm. This distance is typically sufficient for a gel and therefore the cells or cell aggregates contained therein to be unable to pass between the columns, but rather to form a stable interface due to its surface tension. It is furthermore important to ensure that the openings are not too narrow, as otherwise the exchange between the channel and the reservoir can be more difficult so that sufficient supply of nutrients to the cells cannot be ensured.

The inlet opening and/or the outlet opening can be formed in the surface of the cell culture carrier, in particular in the side of the cover element which is disposed opposite to that side on which the base element is attached and in which the depression is formed. Proceeding from the inlet opening and/or the outlet opening, the channel can run at least in part perpendicular to the surface of the cell culture carrier.

This orientation of the channel represents a further contribution to simple and efficient manufacture of a cell culture carrier, in particular when the cover element is manufactured by way of injection molding. In particular, it is relatively easy using injection molding to form elements that run horizontally and/or vertically to a surface, whereas elements that run diagonally or otherwise are difficult or impossible to form. The formation of channels running vertically at least part, in particular also in combination with sections in the form of trenches, is therefore advantageous for injection molding processes.

The channel formed in the cell culture carrier can be made of sections that are parallel or perpendicular to the surface. On the one hand, this can apply to the case in which the channel is configured entirely as a tube in the sample carrier. In particular, the channel can also made in part of a tube and in part of a covered trench in the cover element. In this case, the covered trench can form the parallel sections, and vertical sections can run perpendicular to the surface of the cover element, as passage holes through the cover element.

The inlet opening and/or the outlet opening can furthermore dispose of a port. These ports at the ends of the channel can be formed to be conical. In particular, the ports can correspond to the Luer standard, where the ports can comprise a female Luer adapter or Luer lock adapter. When used as intended, a device for filling the channel through the ports can then comprise a male Luer adapter or Luer lock adapter.

Due to the use of conical ports, in particular ports that correspond to the Luer standard, the ports can be connected in a liquid-tight manner when filling, and the filling process can therefore be carried out in a simple and reliable manner. In addition, the cell culture carrier is compatible with most devices for filling, as the Luer standard is widely used in this context.

The cover element can be a plastic carrier. It can comprise in particular plastic materials such as COC (cyclo-olefin copolymer), COP (cyclo-olefin polymer), PC (polycarbonate), PS (polystyrene), PE (polyethylene), PMMA (polymethyl methacrylate) or transparent thermoplastic material or an elastomer. The cover element can have been produced in particular by injection molding. However, the cover element according to this specification is not restricted to said materials and manufacturing methods.

Due to the use of the materials and methods mentioned, the cell culture carriers can be produced inexpensively and in large numbers having uniform quality. The reason for this is that injection molding with plastic materials is an established and reliable process and is particularly applicable in the case of the plastic materials mentioned. The use of transparent plastic material is particularly advantageous for being able to conduct optical examinations in the cell culture carrier, for example, by way of microscopy.

The base element can comprise plastic material and/or glass. COC, COP, PC, PS, PE, PMMA or other transparent plastic materials, in particular thermoplastic materials, can be used as plastic materials. In particular, the base element can also be configured in the form of a film. In this case, the base element can comprise a material that has the birefringence and autofluorescence of a Schott cover glass (such as D 263 M Schott glass, no. 1.5H (170+/−5 μm)).

Such optically high-quality plastic material can enable microscopic examinations with high precision and low optical imperfections, especially when using microscopy. For example, inverse microscopy can be carried out on the cell culture carrier. A lens is directed onto the cell culture carrier from below and the examination is conducted through the base area or through the base element of the cell culture carrier, respectively. In this case, the high-quality optical properties of the base element mentioned are advantageous for obtaining microscopic images with high resolution and few imaging errors.

As described, the base element can be attached to the cover element by adhesive bonding. In particular, dispersion adhesives or double-sided adhesive tapes can be used in this case. Accordingly, the adhesive film can comprise or be made of dispersion adhesives or double-sided adhesive tapes.

The base element is connected to the cover element such that the optical properties of the cell culture carrier are retained and microscopy, in particular fluorescence microscopy or inverse microscopy, can be carried out using the cell culture carrier. In this case, high resolution must be obtained, in particular in the region of the reservoir and possibly the channel, in order to be able to examine or microscope the cells in the cell culture carrier appropriately. At the same time, these methods are established in the framework of plastic components and represent an inexpensive and efficient way of reliably attaching the base element to the cover element.

The importance of the adhesive film not covering the depression in the cover element is revealed at this point. This would result in the adhesive film being arranged between the reservoir and the base area of the cell culture carrier when used according to the invention. However, an adhesive film typically does not have sufficient optical properties, unlike the base element, for carrying out high-resolution microscopy through the adhesive film because imaging errors would be induced.

The cover element can have a thickness of 0.5 mm to 5 cm, in particular 5 mm to 2 cm. The thickness there is the vertical distance between an upper side and an underside of the cover element. The base element can have a thickness between 1 μm and 2 mm, in particular between 1 μm and 300 μm. A definition analogous to that for the cover element should be applied for the thickness of the base element.

In particular, the base element can be configured as a film that is attached to the cover element. A small thickness of the base element has the advantage that the lens during inverse microscopy can be approached particularly close to a region to be observed in the cell culture carrier. This allows for improved optical resolution.

In addition, the present invention comprises a cell culture carrier kit. This cell culture carrier kit comprises:

A cover element comprising a trench and a depression, where the depression has at least two openings arranged next to one another, and where the trench is connected to the depression by the at least two openings an adhesive film; and a base element, where the base element can be attached to the sample carrier by way of the adhesive film such that the depression and the trench are covered with the base element, and where the assembly of the cell culture carrier kit results in a cell culture carrier described.

In this case, the cell culture carrier kit comprises all the components for a cell culture carrier according to the invention so that a user can prepare the cell culture carrier in a correspondingly versatile manner and then assemble it himself. For example, the depression in the cover element can first be filled with a gel containing cells or cell aggregates, the adhesive film can be attached thereafter to the cover element, and finally the cell culture carrier can be closed with the base element. The advantages discussed in the context of the cell culture carrier therefore also apply to the cell culture carrier kit.

The cell culture carrier can consist of said components, i.e. the cover element, the base element, and the adhesive film.

The adhesive film can be covered with a protective film on at least one side.

Since the adhesive film can be present separately in the cell culture carrier kit, the protective film prevents the adhesive film from being able to adhere to other components. The protective film can itself be in particular non-adhesive, i.e. not adhere to any element other than the adhesive film, and can be easily removed from the adhesive film by the user.

The adhesive film can be applied to the cover element so that the depression and the trench are not covered with the adhesive film, and where the side of the adhesive film facing away from the cover element is covered with a protective film.

This configuration is particularly user-friendly because it is difficult to apply the adhesive film accurately in a manual manner due to the stated sizing of the adhesive film. A user can now use the sample carrier directly without having to apply the adhesive film himself. The protective film can be removed for assembly and the cover element and the base element can finally be joined together.

The present invention beyond that comprises a method for introducing cells or cell aggregates into a cell culture carrier. The method comprises the following steps of:

- providing a previously described cell culture carrier kit;
- filling the depression in the cover element with a gel containing cells or cell aggregates;
- covering the depression and the trench with the base element,
- where the cover element and the base element are connected to one another in a planar manner,
- where the depression and the trench are covered with the base element, and
- where covering the depression is performed after the depression has been filled.

Once the method described has been carried out completely, a previously described cell culture carrier is obtained, into the reservoir of which a gel with cells or cell aggregates has been introduced. The method in connection with the cell culture carrier kit described provides the advantages mentioned in this specification.

The openings of the reservoir can be formed to be so narrow that the cells or cell aggregates in the reservoir cannot escape from the reservoir through the openings.

The advantage is that it is possible to retain the cells in a defined volume, in this case the reservoir, without having to adhere the cells to an inner wall of the reservoir. This is necessary for the reason that certain cell types, such as immune cells, can change their properties due to adhesion to a surface. The cells cannot be flushed out of the reservoir even if a cell medium is exchanged.

The size of the openings can there be adapted accordingly to a cell type used. For example, the size of the openings can be smaller than the size of the cell structures so that the cells cannot pass through the openings. When using a gel, there is the additional effect that the gel can form a stable interface due to its surface tension. In this case, the size of the openings can be adapted accordingly to the properties of the gel so that its surface tension prevents it from being able to pass through the openings.

In the method described, the gel can be filled into the depression using 3D printing.

The use of 3D printing for filling the depression with a gel has the advantage that, firstly, the filling process can be run in an automated manner. This typically entails good reproducibility and efficiency, for example, in the form of time savings over other methods, especially manual ones. Secondly, 3D printing can also form random structures with high precision and the gel can therefore be introduced into the depression in a particularly controlled manner. The cell culture carrier is compatible, in particular, with the use of 3D printing.

The method described can also comprise the step of connecting the inlet opening and the outlet opening of the channel to a perfusion so that a cell medium flows through the channel.

This configuration represents a use according to the invention of the cell culture carrier. The cell medium supplies the cells in the reservoir with nutrients without simultaneously exposing them to a direct flow. This finally allows non-adherent cells in the reservoir to be examined over a sufficiently long period of time. The supply of nutrients is essential for this, as otherwise the cells could die prematurely.

If the cell culture carrier comprises more than one channel, one or more channels can be connected to the perfusion. It is also possible for the channels to be connected to different perfusions and/or for different cell media to flow through different channels and/or at different times.

BRIEF DESCRIPTION OF THE FIGURES

Further features and advantages shall be explained below using the exemplary figures, where.

Hereinafter and in the figures, the same reference characters shall be used for the same or corresponding elements in the various embodiments, unless otherwise specified.

DETAILED DESCRIPTION

Figure 1:
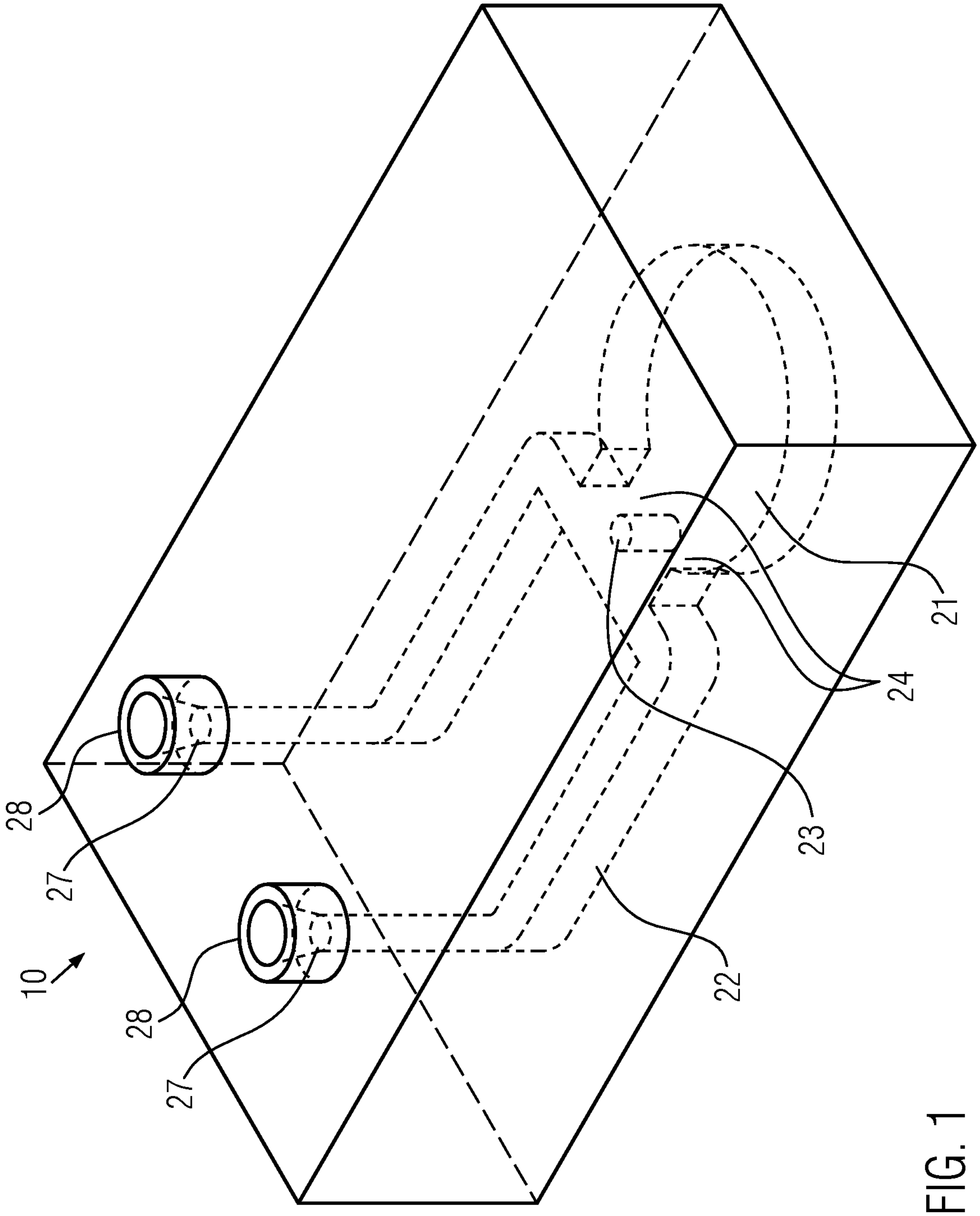
FIG. 1 shows a schematic oblique view of a cell culture carrier according to a first embodiment.

FIG. 1 illustrates the various elements of a cell culture carrier 10 according to the present invention. Cell culture carrier 10 is illustrated in an oblique view. In this case, cell culture carrier 10 has the shape of a cuboid with an underside formed to be planar and comprises or consists of a transparent material, in particular one of the plastic materials COC, COP, PC, PS, PE, PMMA mentioned in this specification or a transparent thermoplastic material or an elastomer. Cell culture carrier 10 shown has a rectangular base area which corresponds to its underside. In principle, the base area of cell culture carrier 10 can also have other shapes, for example, polygonal in some other way or with rounded corners and/or edges. Disposed opposite the underside is the upper side of cell culture carrier 10.

A planar side is particularly advantageous for optical examination. For example, a planar underside is required in microscopy to reduce or prevent optical imaging errors such as astigmatism or spherical aberrations.

In the interior of cell culture carrier 10, reservoir 21 is configured in the form of a cylindrical cavity, i.e. one that is circular in cross section, and has a bottom and a top. As described hereafter, the shape of the cavity is not restricted to a cylindrical geometry. Cylindrical reservoir 21 has a jacket surface which is referred to hereafter as the side wall. Disposed in this side wall are two adjacent openings 24 separated by a barrier or column 23 arranged therebetween. In the present example, this column 23 has a round cross section, but other cross-sectional shapes are also conceivable, for example, elliptical, rectangular or otherwise polygonal.

Cell culture carrier 10 furthermore comprises a channel 22 which is formed in the interior of cell culture carrier 10 as a tube. Formed in the upper side of cell culture carrier 10 are an inlet opening 27 and an outlet opening 27, each in the shape of a hole. Since inlet opening 27 and outlet opening 27 in principle can be used both as an inlet and as an outlet, both are provided with the same reference character. In addition, the two holes are provided with a port 28. Channel 22 therefore runs within cell culture carrier 10 between inlet opening 27 and outlet opening 27. Starting from inlet opening 27 and outlet opening 27, the channel initially runs perpendicularly to the upper side through cell culture carrier 10. In a plane parallel to the base area in which also reservoir 21 is arranged, channel 22 runs horizontally through cell culture carrier 10.

More precisely, the diameter of channel 22 in this example corresponds to the height of reservoir 21. The height of reservoir 21 is the distance between the bottom and the top, and channel 22 and reservoir 21 are disposed in the same plane within cell culture carrier 10. However, the diameter of channel 22 and the height of reservoir 21 need not be identical. The height of reservoir 21 can be greater than the diameter of channel 22 or vice versa.

Channel 22 is connected to reservoir 21 by the two adjacent openings 24. A liquid flowing through channel 22 can therefore enter through openings 24 into reservoir 21. Openings 24 are arranged such that they are aligned to be perpendicular to the direction of flow of a liquid flowing in channel 22. In this way it can be achieved that no direct flow is directed from channel 22 into reservoir 21, but that an exchange between reservoir 21 and channel 22 only takes place by way of diffusion. The width of openings 24 being able to typically be smaller than the diameter of channel 22 can also contribute to this effect. In general, openings 24 are arranged laterally in channel 22 so that they are not disposed in the direction of flow. An alignment perpendicular to the direction of flow represents a special case.

Ports 28 shown in the figure are conical and correspond in particular to the Luer standard. Both of the ports 28 are female Luer ports. When connecting an appropriate device (not shown) to flush channel 22 with a medium, this facilitates a liquid-tight and efficient connection between ports 28 and the device. Accordingly, the device can be fitted with a male Luer adapter or Luer lock adapter.

The specific selection of the height, length, and width of cell culture carrier 10, as well as the shape, volume and specific embodiment of reservoir 21 and channel 22 can be determined according to the respective use of cell culture carrier 10. For example, a rectangular shape, which is based on a typical slide used in microscopy, can be advantageous when examining cell culture carrier 10 under a microscope. The shape and the volume of reservoir 21 and the number, width, and spacing of openings 24 can be optimized, for example, for the cells or cell aggregates to be introduced therein. Likewise, cell culture carrier 10 is not restricted to one channel 22 shown. A second channel or more than two channels can also be present, as can be seen in the embodiments described hereafter.

FIG. 2A-FIG. 2D show different embodiments of channels 22 formed in cell culture carrier 10 and a reservoir 21 as a top view. In this case, cell culture carrier 10 itself has a rectangular base area, but this is not to be understood to be restrictive. The embodiments shown for reservoir 21 and channels 22 can be combined with other shapes of cell culture carrier 10. These embodiments can be combined in particular with the embodiments of a cell culture carrier 10 shown in FIG. 1, FIG. 3, and FIG. 4A.

Figure 2A:
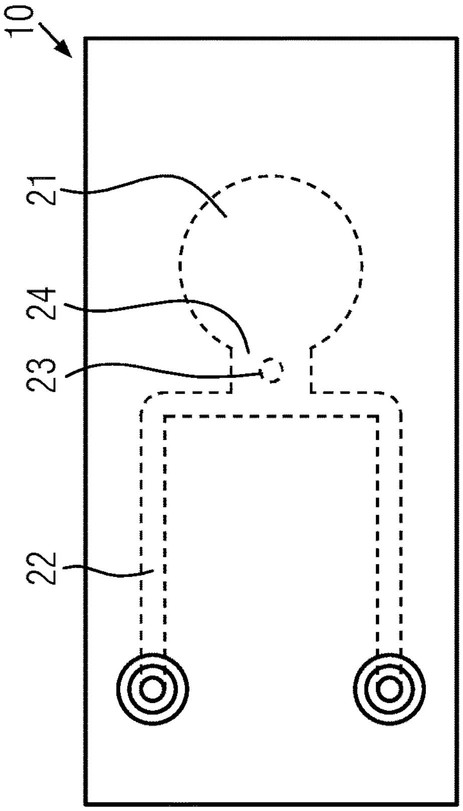
FIG. 2A-FIG. 2D show different embodiments of channels formed in the cell culture carrier and the reservoir as a top view.

According to the embodiment shown in FIG. 2A cell culture carrier 10 comprises a reservoir 21 with a circular cross section as well as a channel 22. This channel 22 is connected to reservoir 21 by two adjacent openings 24. Two openings 24 are separated by a single column 23. In the example shown, channel 22 has a U-shape, in which the inlet opening and the outlet opening of channel 22 are arranged on the same side of reservoir 21. Other arrangements of channel 22 with respect to reservoir 21 are also possible. For example, a channel 22 can run in a straight line and be connected to reservoir 21, where the inlet opening and the outlet opening of channel 22 are arranged on different sides of reservoir 21.

Figure 2B:
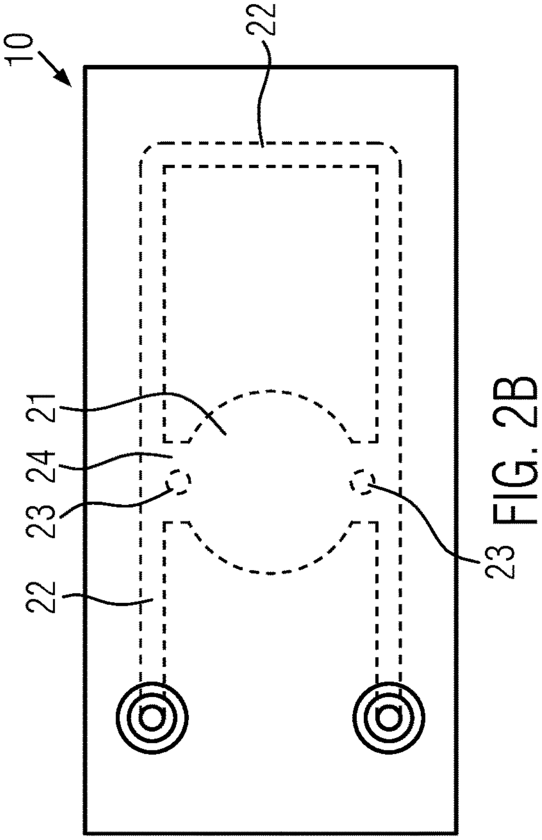

Reservoir 21 has a circular cross section in FIG. 2B. A channel 22 is formed in cell culture carrier 10 and contacts reservoir 21 at two oppositely disposed points, the so-called points of contact. Channel 22 is connected to reservoir 21 by openings 24 at these points of contact. Such designation can also be applied to the other embodiments. However, it is also possible that the points of contact between channel 22 and reservoir 21 are disposed at points other than those shown. The points of contact in a different configuration can be arranged on reservoir 21, as long as they respect the definition of oppositely disposed points mentioned in this specification. Disposed at said points of contact in the side wall of reservoir 21 are two adjacent openings 24 separated by a column 23. This example shows a single column 23, but a plurality of columns 23 and a plurality of openings 24 can also be present.

Figure 2C:
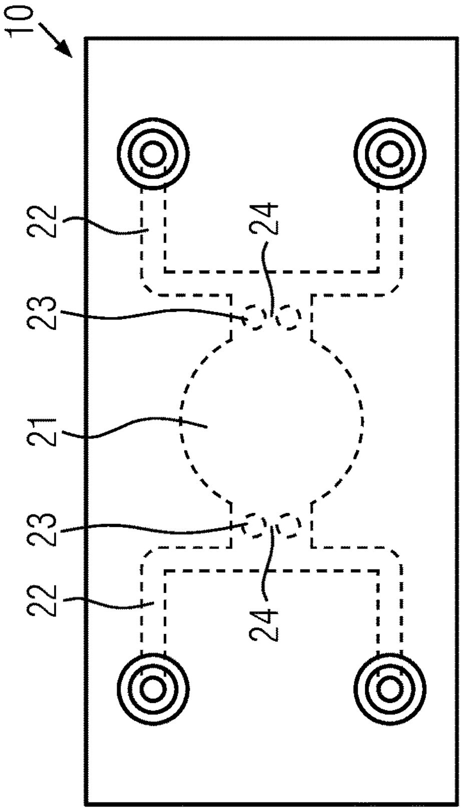

FIG. 2C shows a further embodiment of said sample carrier 10 comprising a reservoir 21 with a circular cross section and two channels 22. Each of two channels 22 is connected to reservoir 21 by three adjacent openings 24. These three openings 24 are separated from one another by two columns 23. Openings 24 in the side wall of reservoir 21 are formed at oppositely disposed points. Furthermore, each of two channels 22 has a U-shape.

Instead of a circular cross section, reservoir 21 in the embodiments shown can have, for example, an elliptical or rectangular cross section. In particular, the combination of two channels 22 is also not restricted to the arrangement of reservoir 21 and channels 22 shown. For example, the openings need not be formed at oppositely disposed points in the side wall of reservoir 21. Likewise, channels 22 can also be formed to have differing shapes, for example, first channel 22 can extend to be U-shaped, whereas second channel 22 is formed as a straight line.

An advantage of this embodiment with two channels is an exchange of a medium or a liquid between channels 22 and reservoir 21 that is accelerated, in particular compared to an embodiment with one channel 22. In addition, the possibility of the development of dead zones, in which exchange does not take place or only on long time scales, is further reduced compared to other regions of reservoir 21.

Figure 2D:
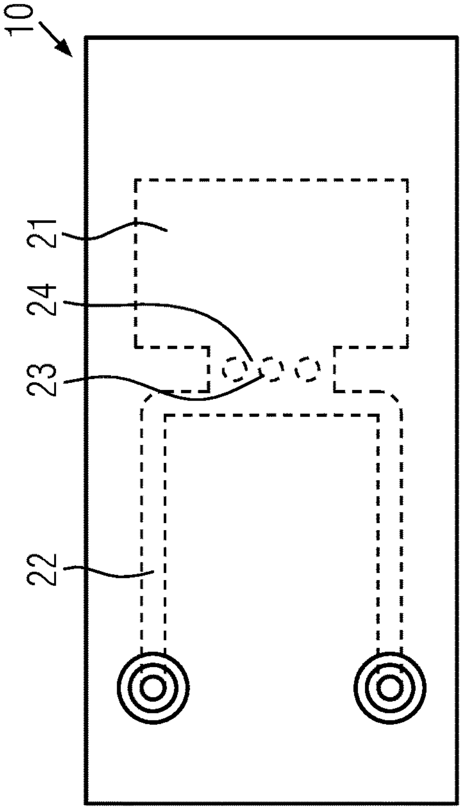

Reservoir 21 in FIG. 2D has a rectangular cross section and a total of four adjacent openings 24 in its side wall. These four openings 24 are separated from one another by three columns 23. A single channel 22 having a U-shape contacts reservoir 21 at the total of four adjacent openings 24.

It is possible for channel 22 to run parallel to reservoir 21 over a relatively long section, in particular in the case of a rectangular reservoir 21. Accordingly, a larger number of openings 24 can be realized in the side wall of reservoir 21. As described, this contributes to a faster and improved exchange of a medium between channel 22 and reservoir 21.

The examples shown in FIG. 2A to FIG. 2D are not restricted to these specific combinations. The shape of the cross section of reservoir 21 can be freely combined with the number and arrangement of one or more channels 22 as well as the number of openings 24. For example, a rectangular reservoir 21 can be formed in cell culture carrier 10 together with two channels 22. The number of openings is also not tied to the number of channels 22 or the cross-sectional shape of reservoir 21.

Figure 3:
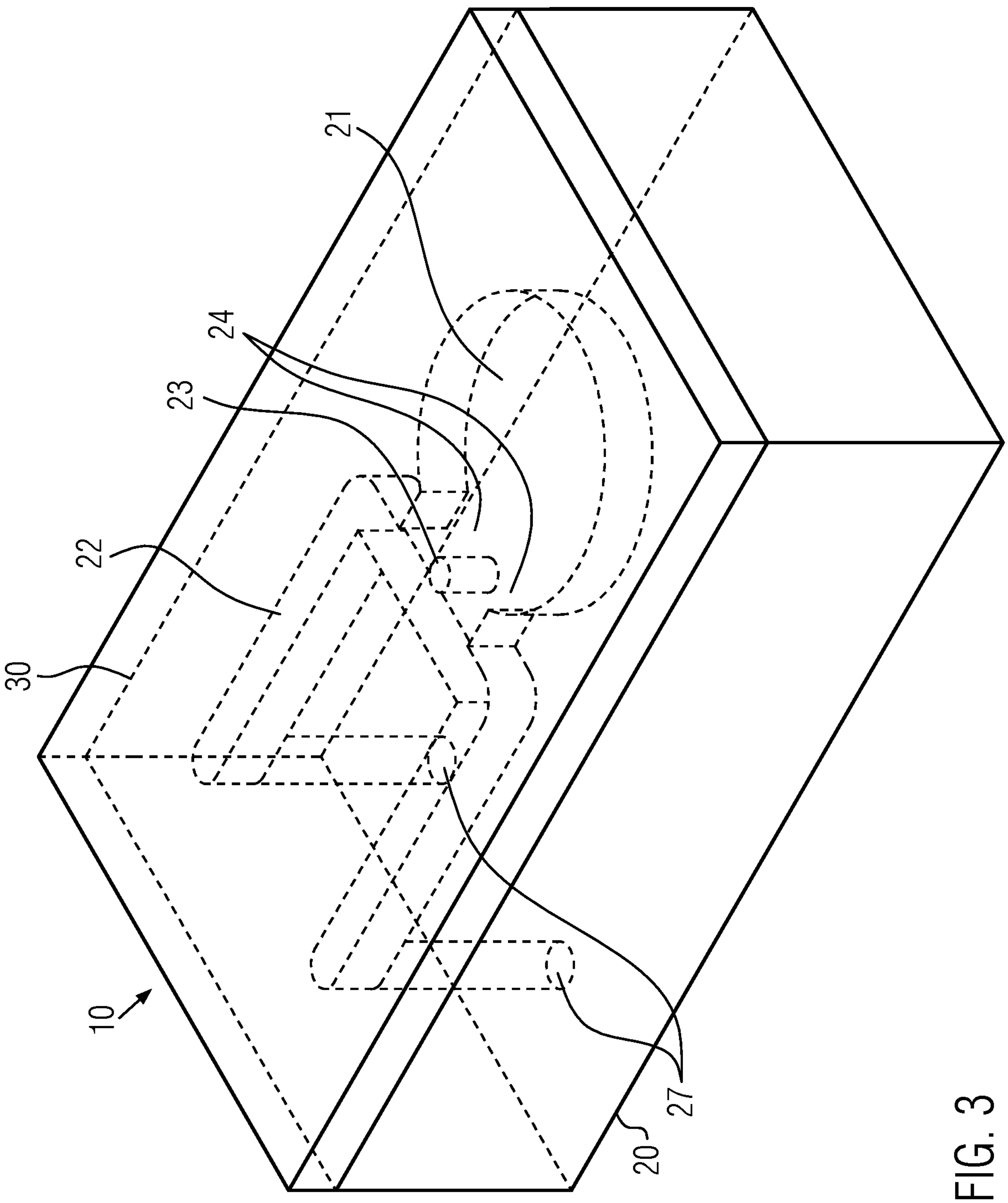
FIG. 3 shows a schematic oblique view of a cell culture carrier according to a second embodiment.

FIG. 3 illustrates the oblique view of a cell culture carrier 10. Cell culture carrier 10 there comprises a cover element 20 and a base element 30. The other elements of cell culture carrier 10 shown correspond to those from the embodiment according to FIG. 1.

The formation of channel 22 and reservoir 21 in cell culture carrier 10 in this embodiment differs from the embodiment according to FIG. 1 in that a trench or a groove-like depression is formed on a surface of cover element 20 that faces the base element. Base element 30 covers the trench and forms a complete channel 22 that runs inside cell culture carrier 10. As shown in the example, channel 22 runs respectively vertically through cell culture carrier 10 at the end of the trench, so that inlet opening 27 and outlet opening 27 are formed on a side of cover element 20 which is disposed opposite to the side in which the trench is formed. In other words, inlet opening 27 and outlet opening 27 are disposed on the side of cover element 20 facing away from base element 30.

Furthermore, cover element 20 comprises a depression formed in the same side of the surface as the trench. The depression is therefore formed in the side of cover element 20 facing base element 30. Like reservoir 21 in the previous embodiment, the depression here has two adjacent openings 24 separated by a column 23 therebetween. The trench is connected to the depression by two openings 24. The depression and the trench can have the same depth in cover element 20, but the trench can also have a greater depth than the depression or vice versa.

The trench is covered with base element 30. In particular, base element 30 can be a transparent film, in particular made of the materials COC, COP, PC, PS, PE, PMMA or other transparent plastic material or a thermoplastic material. In particular, this film can have the autofluorescence and birefringence of a Schott cover glass. The trench is covered such that a liquid flowing through channel 22 cannot escape at the trenches. The covering with base element 30 is therefore liquid-tight.

In addition, the depression is also simultaneously covered with base element 30 so that the former is also closed in a liquid-tight manner. Reservoir 21 is formed within cell culture carrier 10 by covering the depression with the base element.

In addition, the complete cell culture carrier 10 is formed by covering with base element 30, i.e. by connecting cover element 20 and base element 30.

Figure 4A:
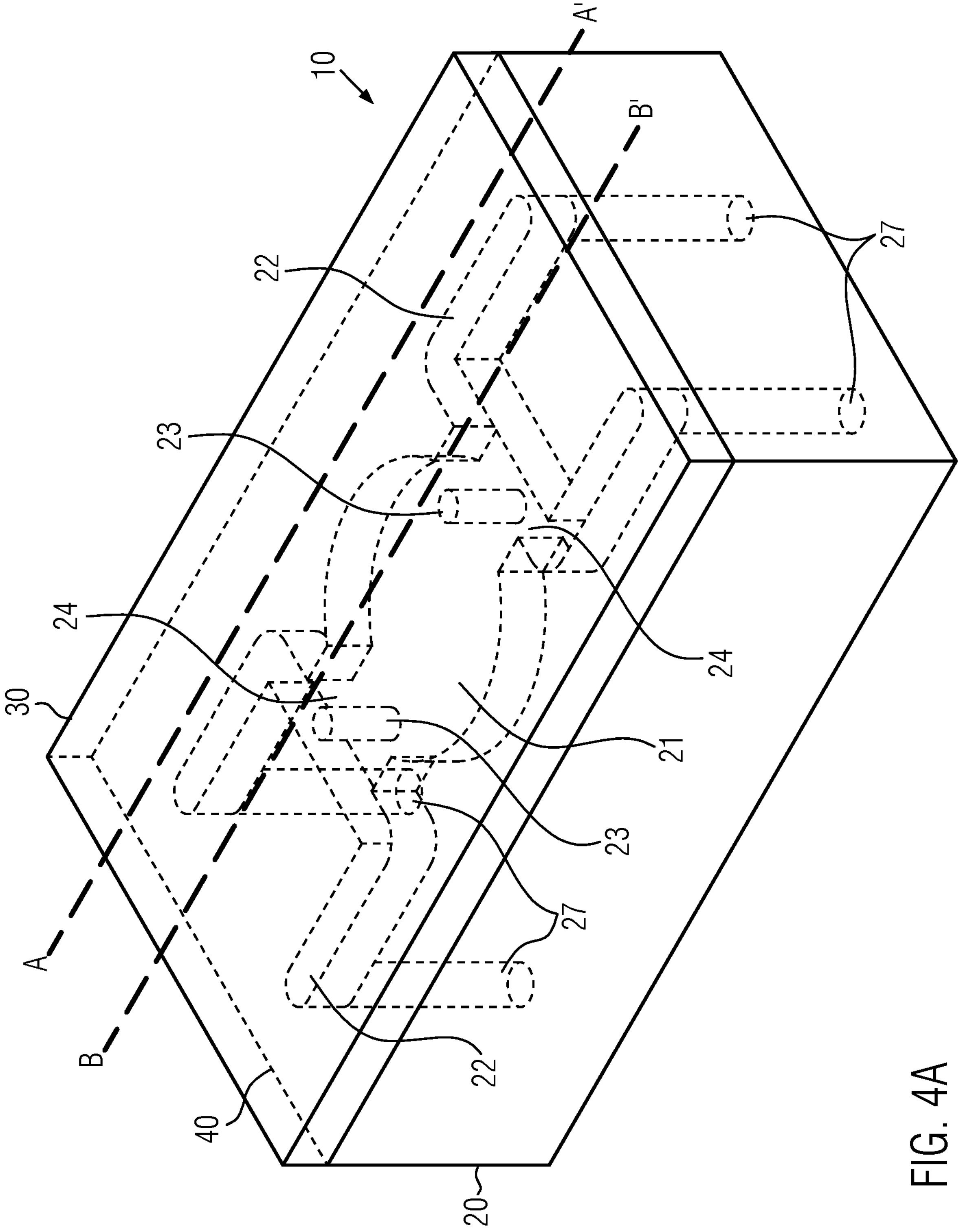
FIG. 4A shows a schematic oblique view of a cell culture carrier according to a third embodiment.

FIG. 4A shows an oblique view of a cell culture carrier 10 according to a further embodiment.

Cell culture carrier 10 shown comprises three elements, a cover element 20, a base element 30, and an adhesive film 40 arranged between cover element 20 and base element 30. Cover element 20 comprises one depression and two trenches. Both trenches are connected to the depression by two adjacent openings 24. The two pairs of adjacent openings 24 are arranged at oppositely disposed points in the depression. Starting out from the trenches, channels 22 continue to run perpendicular to the surface and through cover element 20 in the shape of a tube. On the side of cover element 20 facing away from the depression, an inlet opening 27 and an outlet opening 27 in the shape of a hole in the surface of cell culture carrier 10 are respectively formed for each channel 22.

The two pairs of openings 24 are each separated by a cylindrical column 23 arranged therebetween. Column 23 has a column height, where the column height defines the length of the cylinder. The depression as well likewise has a height defined as the vertical distance between the base of the depression and the surface of cover element 20. In the example shown, the column height of both columns 23 is greater than the height of the depression so that columns 23 project beyond the surface of cover element 20.

As described, an adhesive film 40 is arranged between base element 30 and cover element 20, and connects and adhesively bonds cover element 20 to base element 30 in a planar manner. Where adhesive film 40 is formed such that it covers a side of the surface of cover element 20 but does not cover the trenches, the depression, openings 24, and columns 23. Adhesive film 40 can cover the entire region described, but it is also conceivable for adhesive film 40 to cover only parts of this area. The decisive factor there is that cover element 20 and base element 30 are adhesively bonded firmly to one another by adhesive film 40. Cover element 30 in this example shown is furthermore also configured to cover the trenches and the depression and to close them in a liquid-tight manner.

The difference between the height of the column and the height of the depression can correspond in particular to the thickness of adhesive film 40. The thickness of adhesive film 40 is its vertical extension perpendicular to the surface of cover element 20. This has the advantage that a tight connection can be established between cover element 20 and base element 30 because columns 23 come to touch base element 30 and create a tight connection. If the column height were less than the sum of the height of the depression and the thickness of adhesive film 40, then the thickness of adhesive film 40 could cause gaps or other distances between cover element 20 and base element 30 through which cells or cell aggregates in reservoir 21 can escape and/or through which the cell medium that can flow through channels 22 can exit. It is also possible for the column height to be greater than the sum of the height of the depression and the thickness of adhesive film 40. In this case, closure the trenches and the depression by base element 30 can be obtained in a liquid-tight manner by way of increased contact pressure. However, this is also no longer possible if columns 23 protrude too far beyond the surface of cover element 20.

As in the previous embodiment, the trenches and the depression are covered with base element 30. As a result, complete channels 22 and reservoir 21 are formed in the interior of cell culture carrier 10.

The figure finally shows two axes A-A' and B-B' which are made reference to in the following FIG. 4B and FIG. 4C.

Figure 4B:
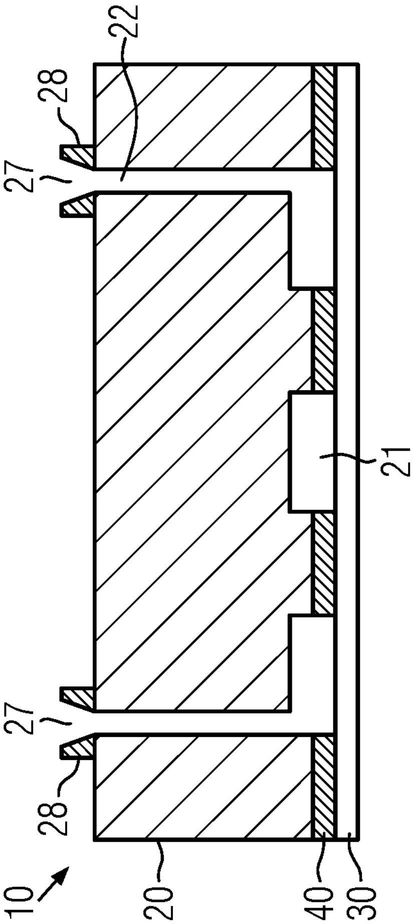
FIG. 4B and FIG. 4C show a cross section of the cell culture carrier in FIG. 4A along two different sectional axes.

FIG. 4B shows a cross section of cell culture carrier 10 from FIG. 4A, where the cut is made along the axis AA' shown in FIG. 4A. Cover element 20 there is illustrated above base element 30, and adhesive film 40 is arranged between cover element 20 and base element 30. Consequently, the trenches and the depression are disposed on the lower side of cover element 20. Inlet opening 27 or outlet opening 27 of first channel 22 as well as inlet opening 27 or outlet opening 27 of second channel 22 are arranged on the upper side. Furthermore, inlet openings 27 or outlet openings 27 illustrated each have a conical port 28 which can correspond in particular to the Luer standard.

Depending on the embodiment of the depression, this does not necessarily have to occur in the cross section shown. For example, the diameter of the circular cross section of the depression can be formed to be so small that no segment of the depression is comprised any longer in the cross section along axis A-A'.

As illustrated, adhesive film 40 covers the lower surface of cover element 20, where the trenches and the depression are not covered with adhesive film 40. The trenches and the depression are covered with base element 30. Base element 30 there forms the lower termination of cell culture carrier 10. Reservoir 21 is formed in cell culture carrier 10 by covering the depression with base element 30.

The fact that base element 30 forms the lower termination of cell culture carrier 10 represents its intended use. For example, inverse microscopy can be carried out on cell culture carrier 10, where an objective is directed from below through base element 30 onto reservoir 21 in cell culture carrier 10.

Figure 4C:
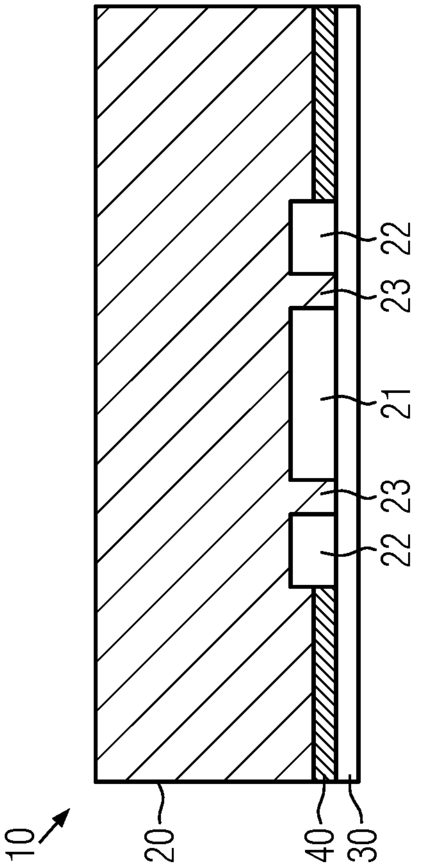

FIG. 4C likewise shows a cross section of cell culture carrier 10 from FIG. 4A, where the cut is made along axis B-B' shown in FIG. 4A. Unlike in FIG. 4B, columns 23 can be seen in this case. As illustrated, columns 23 are formed in cover element 20 and project beyond the surface of cover element 20. Columns 23 are therefore greater in height than the reservoir and the trenches. In addition, columns 23 touch base element 30, accordingly no adhesive film 40 can be arranged on columns 23. Reservoir 21 and channels 22 in cell culture carrier 10 are formed by covering the depression and the trenches with base element 30.

Figure 5:
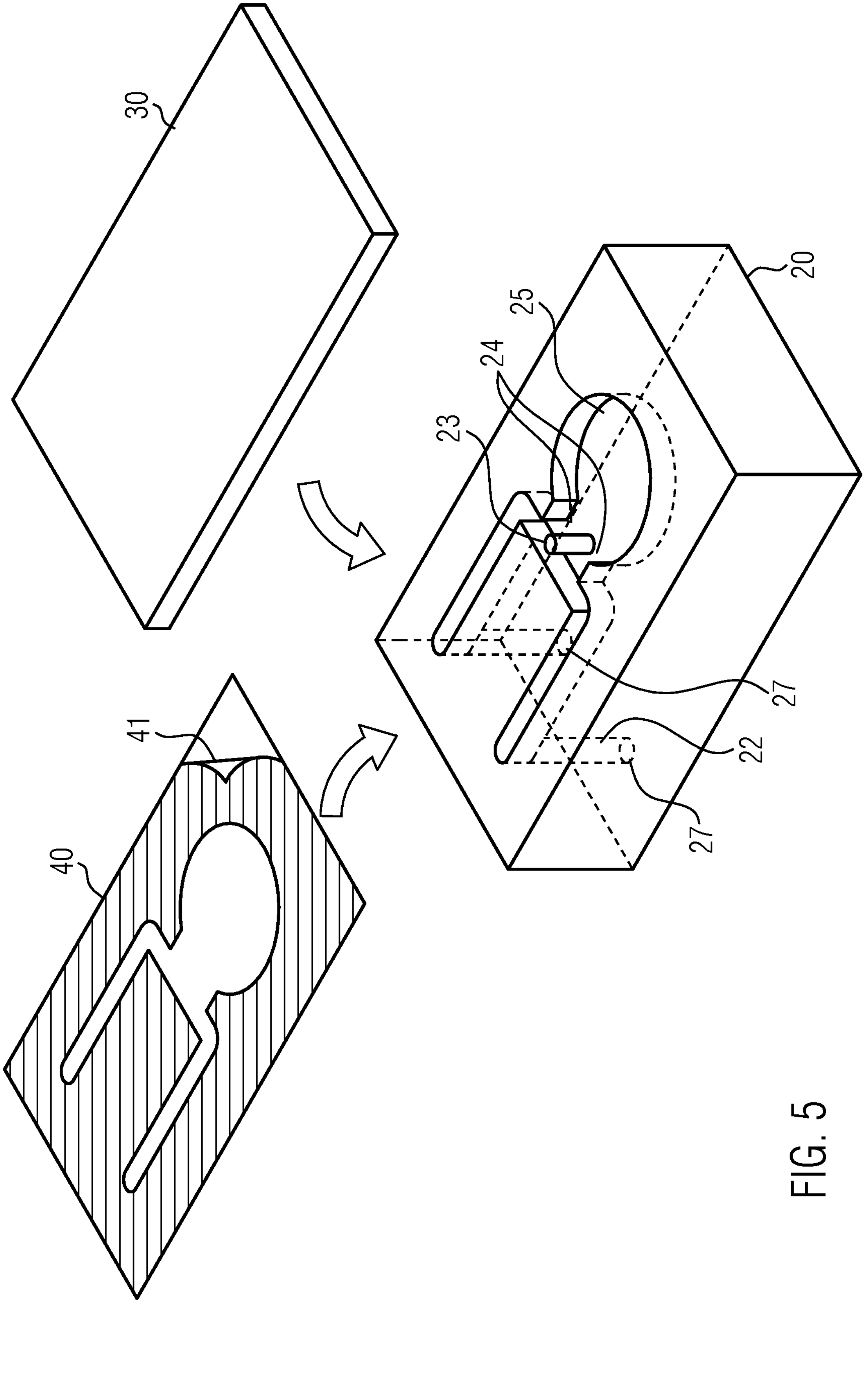
FIG. 5 shows a cell culture carrier kit.

A cell culture carrier kit according to the present invention is shown in FIG. 5. It first comprises a cover element 20 having formed therein a depression 25 of circular cross section, two adjacent openings 24 in one side wall of depression 25, where openings 24 are separated by a cylindrical column 23, as well as a trench. Depression 25 and the trench are formed in the same side of the surface of cover element 20. A channel 22 adjoins each of the two ends of the trench and is formed as a tube in cover element 20 and runs perpendicular through cover element 20 as a passage opening. In addition, an inlet opening 27 and an outlet opening 27 of channel 22 are arranged in the side of the cover element 20 facing away from depression 25. Like in the embodiment according to FIG. 4A, column 23 projects beyond the surface of base element 20.

Separately from cover element 20, the kit furthermore comprises an adhesive film 40 which can be attached to the surface of cover element 20 on which depression 25 and the trench are also formed. Adhesive film 40 comprises a recess whose shape corresponds to the outline of depression 25 and of the trench in the surface of cover element 20. Furthermore, adhesive film 40 can be covered with a protective film 41 on at least one side, in particular on both sides. The purpose of this protective film 41 is that adhesive film 40 can be stored separately and does not adhere to any other object. Before adhesive film 40 is attached to cover element 20, protective film 41 would have to be removed.

Finally, the kit also comprises a base element 30 that can be applied to cover element 20 and to adhesive film 40. In particular, base element 30 can be a film. Together, the parts described result in a complete cell culture carrier 10 as described which is intended for the use described in this specification and has the properties mentioned.

The considerations presented in this specification with regard to the specific shape and selection of materials apply in particular for the specific properties of cover element 20 and base element 30. Furthermore, the combinations options mentioned in this specification apply in particular to base element 20, for example, with regard to the number and the arrangement of channels 22 and the shape of depression 25. In this case, the shape of adhesive film 40 must be adapted accordingly so that, when the kit is assembled, the trenches, depression 25, openings 24, and columns 23 are not covered with adhesive film 40 also in other embodiments of cover element 20. The specific configuration of the cell culture carrier kit is therefore not restricted to a combination of cover element 20 shown with a corresponding adhesive film 40 and a cover element 30.

For the assembly of the kit, adhesive film 40 is first applied to cover element 20, specifically to the side in which depression 25 and the trench are formed. If the adhesive film is covered on both sides with a protective film 41, then protective film 41 must first be removed on one side. Once adhesive film 40 has been applied, adhesive film 40 covers neither depression 25, nor openings 24, nor columns 23, nor the trench. Finally, base element 30 is applied to cover element 20 and to adhesive film 40 so that cover element 20 and base element 30 are connected and adhesively bonded to one another in a planar manner, and the trench and depression 25 are covered with base element 30. Channel 22 and reservoir 21 are formed in this way. After assembly of the kit, a complete cell culture carrier 10 according to the present invention is obtained.

Figure 6B:
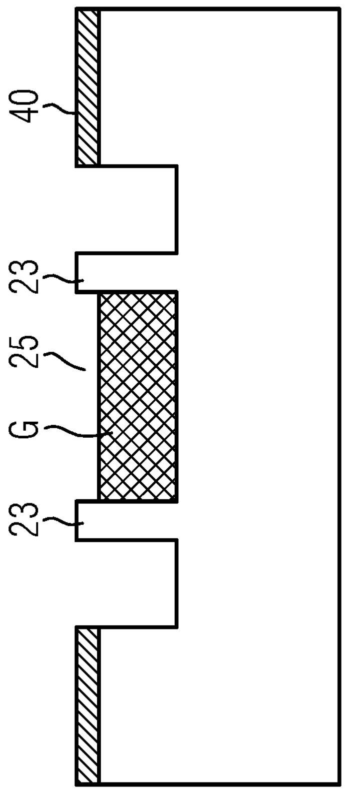
FIG. 6A to FIG. 6C show a method for introducing cells or cell aggregates into a cell culture carrier.
Figure 6A:
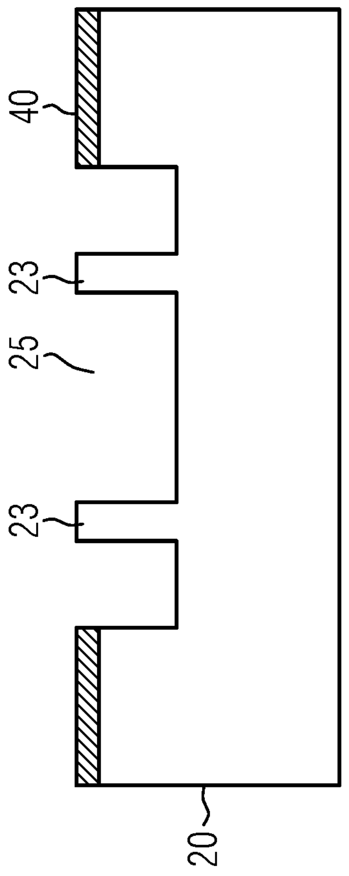
Figure 6C:
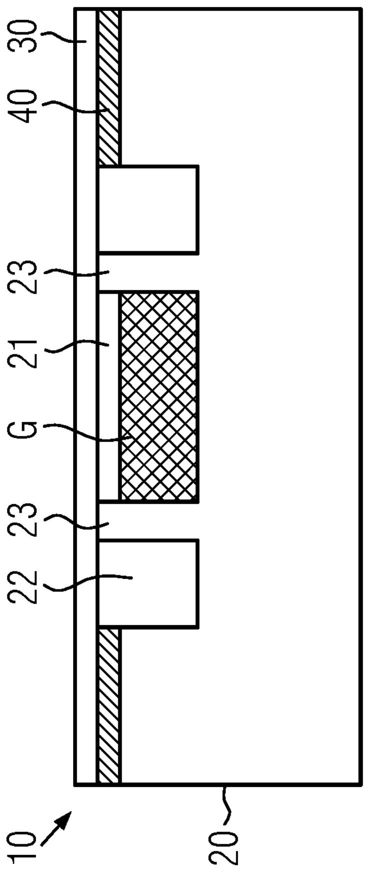

A method for introducing cells or cell aggregates into a cell culture carrier 10 is shown in FIG. 6A to FIG. 6C. The individual figures show a cross section of the cell culture carrier kit shown in FIG. 5 after various steps of the method. The cut was carried out analogously to axis B-B' in FIG. 4A. Accordingly, the cell culture carrier kit initially comprises a cover element 20 with a depression 25 and at least one trench in the surface of cover element 20. Furthermore, depression 25 comprises at least two pairs of two openings each in its side wall which are arranged at oppositely disposed points in the side wall and are separated by a column 23. Correspondingly, cover element 20 comprises two columns 23 which can be seen in the cross section shown. Columns 23 therefore project beyond the surface of cover element 20. An adhesive film 40 is applied to cover element 20, where adhesive film 40 does not cover depression 25, the trenches, and columns 23.

In the first step of the method, as shown in FIG. 6A, a cover element 20 of a cell culture carrier kit is first provided, where adhesive film 40 is already attached onto cover element 20.

According to FIG. 6B, depression 25 is then filled with a gel G containing cells or cell aggregates. Gel G can be filled in until depression 25 is completely filled. This corresponds to a maximum filling level. However, this is not necessarily the case. It is also possible for depression 25 to be filled to any level below the maximum filling level, as shown in FIG. 6B. In addition, it is not absolutely necessary for the entire cross-sectional area of depression 25 to be used for filling with gel G. For example, a small amount of gel G can be introduced into the center of depression 25, where a diameter of the gel structure introduced in this manner is smaller than the diameter of depression 25 and/or the height of depression 25. Filling depression 25 with gel G can be carried out in particular by way of 3D printing or using a 3D printer, respectively. For this purpose, a needle of the 3D printer is inserted into depression 25 from above and gel G is printed accordingly into depression 25. An advantage of using a 3D printer is the precise or detailed and reproducible formation of a gel structure in depression 25.

In a next step, depression 25 is covered with base element 30 so that reservoir 21 is formed. The trenches are also covered at the same time so that channels 22 are formed and now run completely within cell culture carrier 10. This step is illustrated in FIG. 6C.

It is to be noted that adhesive film 40 does not have to be applied to cover element 20 at the beginning of the method. Instead, adhesive film 40 can also be attached onto cover element 20 in a dedicated method step. This method step must be carried out before cell culture carrier 10 is finally closed.

The method described can be carried out together with the cell culture carrier kit mentioned in this specification. There are no restrictions regarding the specific configuration of reservoir 21 and of the trench or of the trenches, respectively. Furthermore, there are no restrictions regarding the number of trenches and/or openings 24 in reservoir 21 or of depression 25, respectively. If applicable, all the embodiments described for the depression and the trench, or for reservoir 21 and channel 22, respectively, can be used in connection with the cell culture carrier kit and the method.

What is claimed is:

1. A cell culture carrier comprising:
a substrate;
a first channel;
a second channel; and
a reservoir,
wherein said first channel, said second channel and said reservoir are formed in the substrate,
wherein said first channel has an inlet opening in an outer side of said substrate and an outlet opening in said outer side of said substrate;
wherein said second channel has an inlet opening in the outer side of said substrate and an outlet opening in said outer side of said substrate;
wherein said reservoir has at least two openings arranged next to one another;
wherein said first channel is connected to said reservoir by said at least two openings,
wherein said second channel is connected to said reservoir by at least two further openings,
wherein said reservoir is connected to the outer side of said substrate by no other channel than the first channel and the second channel,
wherein the at least two openings and the at least two further openings are arranged laterally in the first channel and second channel respectively, such that the first channel, the second channel, the at least two openings, and the at least two further openings are located on a same plane, and
wherein an exchange between the reservoir and the first channel as well as between the reservoir and the second channel only takes place by way of diffusion.

2. The cell culture carrier according to claim 1, wherein said at least two openings between said reservoir and said first channel and said at least two further openings between said reservoir and said second channel are arranged at oppositely disposed points in said reservoir.

3. The cell culture carrier according to claim 1, wherein a distance between two of said at least two openings is greater than half the value of a width of one of said at least two openings and/or smaller than five times the value of the width of one of said at least two openings.

4. The cell culture carrier according to claim 1, wherein said reservoir is coated in part or entirely with a cell-repellent layer.

5. The cell culture carrier according to claim 1, wherein said substrate comprises
a cover element, and
a base element,
wherein a trench and a depression are formed on a first side of said cover element facing said base element,
wherein said cover element and said base element are connected to one another in a planar manner such that said trench and said depression are covered with said base element, and
wherein said first channel is formed by covering said trench, and said reservoir is formed by covering said depression.

6. The cell culture carrier according to claim 5 further comprising an adhesive film which is arranged between said cover element and said base element so that said cover element and said base element are connected and adhesively bonded to one another in a planar manner.

7. The cell culture carrier according to claim 5, wherein two of said at least two openings arranged next to one another of said first channel are separated by a column,
wherein said column is formed in said cover element and touches said base element, and
wherein a side of said base element facing said cover element is formed to be planar.

8. The cell culture carrier according to claim 1, wherein said reservoir is filled with a gel containing cells or cell aggregates.

9. A cell culture carrier kit comprising:
a cover element comprising:
a trench; and
a depression,
wherein said depression has at least two openings arranged next to one another; and
wherein said trench is connected to said depression by said at least two openings;
an adhesive film; and
a base element;
wherein said base element is attachable to said cover element by way of said adhesive film such that said depression and said trench are covered with said base element to form a substrate comprising a reservoir and a first channel and a second channel, and
wherein the assembly of said cell culture carrier kit results in a cell culture carrier comprising:
the substrate;
the first channel;
the second channel; and
the reservoir,
wherein said first channel, said second channel, and said reservoir are formed in the substrate,
wherein said first channel has an inlet opening in an outer side of said substrate and an outlet opening in said outer side of said substrate,
wherein said second channel has an inlet opening in the outer side of said substrate and an outlet opening in said outer side of said substrate,
wherein said reservoir has the at least two openings arranged next to one another,
wherein said first channel is connected to said reservoir by said at least two openings,
wherein said second channel is connected to said reservoir by at least two further openings,
wherein said reservoir is connected to the outer side of said substrate by no other channel than the first channel and the second channel, wherein the at least two openings and the at least two further openings are arranged laterally in the first channel and second channel respectively, such that the first channel, the second channel, the at least two openings, and the at least two further openings are located on a same plane, and wherein an exchange between the reservoir and the first channel as well as between the reservoir and the second channel only takes place by way of diffusion.

10. The cell culture carrier kit according to claim 9, wherein said adhesive film is applied to said cover element so that said depression and said trench are not covered with said adhesive film, and wherein a side of said adhesive film facing away from said cover element is covered with a protective film.

11. A method for introducing cells or cell aggregates into a cell culture carrier comprising:

providing a cell culture carrier kit comprising:

a cover element comprising a trench and a depression, wherein said depression has at least two openings arranged next to one another, and wherein said trench is connected to said depression by said at least two openings;

an adhesive film; and a base element;

filling said depression in said cover element with a gel (G) containing cells or cell aggregates; and covering said depression and said trench with said base element to form a substrate comprising a reservoir, a first channel, and a second channel, wherein said cover element and said base element are connected to one another in a planar manner, wherein said base element is attached to said cover element by way of said adhesive film such that said depression and said trench are closed with said base element, wherein covering said depression is performed after said depression has been filled, and wherein assembly of said cell culture carrier kit results in a cell culture carrier comprising:

the substrate;

the first channel;

the second channel; and the reservoir, wherein said first channel, said second channel, and said reservoir are formed in the substrate, wherein said first channel has an inlet opening in an outer side of said substrate and an outlet opening in said outer side of said substrate, wherein said second channel has an inlet opening in the outer side of said substrate and an outlet opening in said outer side of said substrate, wherein said reservoir has the at least two openings arranged next to one another, wherein said first channel is connected to said reservoir by said at least two openings, wherein said second channel is connected to said reservoir by at least two further openings, wherein said reservoir is connected to the outer side of said substrate by no other channel than the first channel and the second channel, wherein the at least two openings and the at least two further openings are arranged laterally in the first channel and second channel respectively, such that the first channel, the second channel, the at least two openings, and the at least two further openings are located on a same plane, and wherein an exchange between the reservoir and the first channel as well as between the reservoir and the second channel only takes place by way of diffusion.

12. The method according to claim 11, wherein said gel (G) is filled into said depression by way of 3D printing.

13. The method according to claim 11, further comprising:

connecting said inlet opening and said outlet opening of said first channel to a perfusion so that a cell medium flows through said first channel.

14. The cell culture carrier kit according to claim 9, wherein said reservoir has a circular, elliptical, or rectangular cross-sectional area, and/or wherein a ratio of two main extensions of the cross section of said reservoir is in the range between 0.5 and 2, and wherein the cross-sectional area is disposed parallel to a base area of said cell culture carrier.

15. The cell culture carrier according to claim 5, wherein the base element is on the first side of the cover element, and wherein the inlet opening and the outlet opening of at least one of the first channel or the second channel are on a second side of the cover element that is opposite the first side.

* * * * *